United States Patent
Crumby et al.

(10) Patent No.: US 8,399,382 B2
(45) Date of Patent: Mar. 19, 2013

(54) COTTON GROWTH REGULATOR

(75) Inventors: Tom I. Crumby, Bolton, MS (US); Joseph P. Reed, North Little Rock, AR (US); Henry R. Mitchell, Louisville, MS (US); Stewart Throop, Bel Air, MD (US); John S. Wilson, Cary, NC (US); John C. Braun, Jr., Wylie, TX (US)

(73) Assignee: FMC Corporation, Philadelphia, PA (US)

( * ) Notice: Subject to any disclaimer, the term of this patent is extended or adjusted under 35 U.S.C. 154(b) by 933 days.

(21) Appl. No.: 12/282,246

(22) PCT Filed: Mar. 13, 2007

(86) PCT No.: PCT/US2007/006301
§ 371 (c)(1),
(2), (4) Date: Sep. 9, 2008

(87) PCT Pub. No.: WO2007/106482
PCT Pub. Date: Sep. 20, 2007

(65) Prior Publication Data
US 2009/0062122 A1  Mar. 5, 2009

Related U.S. Application Data

(60) Provisional application No. 60/782,150, filed on Mar. 14, 2006.

(51) Int. Cl.
*A01N 43/653* (2006.01)
(52) U.S. Cl. ...................................................... 504/273
(58) Field of Classification Search .................... None
See application file for complete search history.

(56) References Cited

U.S. PATENT DOCUMENTS

| 5,125,958 A | 6/1992 | Poss |
| 2005/0221985 A1* | 10/2005 | Garcia et al. .................. 504/128 |

OTHER PUBLICATIONS

Brown et al. "Weed Control programs for minimum-tillage cotton", Weed Science (1985), vol. 33, No. 6, pp. 843-847, abstract. Source: Database CAPlus on STN AN:1986:2141.
Bar'Etas et al. "Effect of defoliants on nitrogen metabolism in cotton fruit organs", (1971), vol. 18, No. 6, pp. 1269-1272, abstract. Source: Database CAPlus on STN AN: 1972:95629.

* cited by examiner

*Primary Examiner* — Alton Pryor
(74) *Attorney, Agent, or Firm* — FMC Corporation

(57) ABSTRACT

Protoporphyrinogen oxidase enzyme-inhibiting compounds are useful in compositions and methods for regulating growth of cotton plants. Of particular interest is the use of carfentrazone ethyl and certain metabolites thereof for regulating growth of cotton plants.

8 Claims, No Drawings

COTTON GROWTH REGULATOR

This application claims the benefit of U.S. Provisional Application No. 60/782,150, filed Mar. 14, 2006.

FIELD OF THE INVENTION

The present invention relates to plant growth regulators for use in cotton production.

BACKGROUND OF THE INVENTION

Cotton is a crop of great importance within the agricultural sector, supplying versatile fiber used for the production of clothing, home furnishings, and other industrial products. Cotton is used for virtually every type of clothing, from coats and jackets to foundation garments. Cotton's uses in home furnishings range from bedding to window shades. Industrial products containing cotton include wall coverings, book bindings, zipper tapes, medical supplies, industrial thread and tarpaulins. Additional cotton products derive from seed processing, including oil and seed meal.

Modern commercial cotton crops grow as vigorous, compact shrubs with a life cycle of just one growing season, bearing little resemblance to their ancestry as tree species of the family Malvacae found in several tropical areas globally. The growing cycle of the various species and varieties of commercial cotton varies in duration, yet despite plant breeding advancements, the sequence of flowering, fruit production and boll opening is fixed. The cotton plant remains intolerant of freezing temperatures and requires a relatively long growing season. Cotton thrives best with conditions of plentiful sunshine and soil moisture early in the growing season, followed by intense heat and ample but not excessive soil moisture as the plant fruits and its bolls fill, ripen and finally open.

The biology of the cotton plant gives context to the cotton industry's technology needs. It is the cotton grower's responsibility to maximize production and quality as weather, insects and other pests adversely impact growing conditions. Cotton growers in temperate climates have particular interest in technologies ensuring production of maximum fiber yields and quality within the period of days each year conducive to cotton growth, referred to as managing for earlier production, or earliness. By redirecting cotton plants energy into filling, ripening and opening mature bolls, rather than in producing new growth, harvesting can be done earlier without loss of yield.

Abnormal weather conditions, such as cool and/or wet conditions in mid-summer may stimulate the cotton plant to produce excessive terminal growth. Terminal growth is defined as new growth at the top of the plant. This may cause significant cotton yield and/or quality losses due to conversion of nutrients and moisture into terminal growth instead of filling and maturing existing bolls, i.e. foliar growth rather than reproductive growth. Such late season terminal growth also makes the cotton plant more susceptible to disease and insect attack. New foliage attracts insects, for example, fall armyworms, which feed on the nutrients within the new leaves, and bollworms and stinkbugs which feed on ripening bolls and cause damage to bolls by destroying seed, staining the lint and in many cases causing the bolls to rot due to secondary infections by plant pathogens.

Herbicides/defoliants and plant growth regulators have been used to completely defoliate cotton plants at harvest time. However, there are currently no means available to cotton growers to remove or control the terminal growth of the cotton plant in such growing conditions. Mechanical control (or 'topping' the cotton plant) is not practiced, and would not be practical given the large scale of modern cotton farming. Without a means to remove or control terminal growth when such situations develop, cotton growers suffer significant monetary losses due to reductions in yield.

SUMMARY OF THE INVENTION

It has now been found that the use of a compound selected from the group consisting of 1) a protoporphyrinogen oxidase enzyme-inhibiting (PPO-inhibiting) compound, 2) a harvest growth regulating (HGR) compound, 3) a cell membrane disruption (CMD) compound or 4) an amino acid synthesis inhibiting (AAS-inhibiting) compound is effective as a cotton plant growth regulator to provide control of terminal growth of cotton plants, improving productivity. Treatment effects from these applications to desirable plant parts are minimal, relative to the benefits. Benefits from controlling terminal growth include maximizing yield, improved quality of cotton fiber produced, reduced insect damage losses and reduction of losses from plant diseases affecting cotton foliage and fruit. Control of cotton plant terminal growth by defoliation or desiccation makes the cotton plant unattractive to insects, for example, gravid fall armyworm female moths, which are looking for succulent new growth to lay eggs and support early instar larvae. A substantial cost savings is realized by not having to apply a late season insecticide for insect control.

Other aspects of the present invention will become apparent from the description below.

DETAILED DESCRIPTION OF THE INVENTION

It has now been found that the use of at least one compound selected from 1) a protoporphyrinogen oxidase enzyme-inhibiting (PPO-inhibiting) compound, 2) a harvest growth regulating (HGR) compound, 3) a cell membrane disruption (CMD) compound or 4) an amino acid synthesis inhibiting (AAS-inhibiting) compound as a cotton plant growth regulator provides control of terminal growth of cotton plants when needed, improving productivity. Specifically, the present invention is a cotton plant growth regulating composition comprising 1) a protoporphyrinogen oxidase enzyme-inhibiting compound in an amount from 0.0005 to 0.025 pound active ingredient per acre, 2) a harvest growth regulating compound in an amount from 0.1 to 1.0 pound active ingredient per acre, 3) a cell membrane disruption compound in an amount from 0.1 to 1.0 pound active ingredient per acre or 4) an amino acid synthesis inhibiting compound in an amount from 0.1 to 1.0 pound active ingredient per acre.

Another aspect of the present invention is a method for controlling terminal growth of a cotton plant, which comprises applying 1) a protoporphyrinogen oxidase enzyme-inhibiting compound in an amount from 0.0005 to 0.025 pound active ingredient per acre, 2) a harvest growth regulating compound in an amount from 0.1 to 1.0 pound active ingredient per acre, 3) a cell membrane disruption compound in an amount from 0.1 to 1.0 pound active ingredient per acre or 4) an amino acid synthesis inhibiting compound in an amount from 0.1 to 1.0 pound active ingredient per acre, or an agriculturally-acceptable salt, ester, acid, or metabolite of such a compound to a cotton plant. Preferably, the application is performed topically on foliage, including the terminal growth, of a cotton plant. The application can be performed at a time between opening of the first cotton boll and opening of the first 40% of all the bolls on the plant.

As set forth above, compositions comprising PPO-inhibiting compounds, and their agriculturally-acceptable salts, esters, acids, and metabolites find utility as chemical growth regulators of cotton plants in the present invention. Examples of PPO-inhibiting compounds which may be used in the present invention include, without limitation, one or more of acifluorfen-sodium, bifenox, chlomethoxyfen, chlornitrofen, ethoxyfen-ethyl, fluorodifen, fluoroglycofen-ethyl, fluoronitrofen, fomesafen, furyloxyfen, halosafen, lactofen, nitrofen, nitrofluorfen, oxyfluorfen, cinidon-ethyl, flumiclorac-pentyl, flumioxazine, profluazol, pyrazogyl, oxadiargyl, oxadiazon, pentoxazone, fluazolate, pyraflufen-ethyl, benzfendizone, butafenacil, fluthiacet-methyl, thidiazimin, azafenidin, carfentrazone-ethyl, sulfentrazone, flufenpyr-ethyl, as well as other PPO-inhibiting compounds, and their agriculturally-acceptable salts, esters, acids, and metabolites. Preferred PPO-inhibiting compounds for use as cotton plant growth regulators are a) pyraflufen-ethyl; ethyl 2-chloro-5-[4-chloro-5-(difluoromethoxy)-1-methyl-1H-pyrazol-3-yl]-4-fluorophenoxyacetate, b) flumiclorac-pentyl; pentyl [2-chloro-4-fluoro-5-(1,3,4,5,6,7-hexahydro-1,3-dioxo-2H-isoindol-2-yl)phenoxy]acetate, c) fluthiacet-methyl; methyl [[2-chloro-4-fluoro-5-[(tetrahydro-3-oxo-1H,3H-[1,3,4] thiadiazolo[3,4-a]pyridazin-1-ylidine)amino]phenyl]thio] acetate, d) carfentrazone-ethyl; ethyl 2-chloro-3-[2-chloro-5-(4-difluoromethyl-3-methyl-5-oxo-4,5-dihydro-[1,2,4]-triazol-1-yl)-4-fluorophenyl]propionate and e) the metabolites of carfentrazone ethyl, namely, i) α,2-dichloro-5-[4-(difluoromethyl)-4,5-dihydro-3-methyl-5-oxo-1H-1,2,4-triazol-1-yl]-4-fluorobenzenepropanoic acid (chloropropanoic acid), ii) 2-chloro-5-[4-(difluoromethyl)-4,5-dihydro-3-methyl-5-oxo-1H-1,2,4-triazol-1-yl]-4-fluorobenzenepropenoic acid (cinnamic acid), iii) 2-chloro-5-[4-(difluoromethyl)-4,5-dihydro-3-methyl-5-oxo-1H-1,2,4-triazol-1-yl]-4-fluorobenzoic acid (benzoic acid), and iv) 2-chloro-5-[4-(difluoromethyl)-4,5-dihydro-3-methyl-5-oxo-1H-1,2,4-triazol-1-yl]-4-fluorobenzenepropanoic acid (propanoic acid). An even more preferred PPO-inhibiting compound for use as a chemical growth regulator is carfentrazone ethyl:

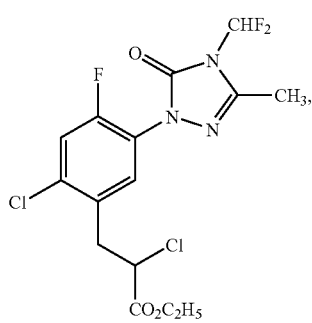

namely ethyl 2-chloro-3-[2-chloro-5-(4-difluoromethyl-3-methyl-5-oxo-4,5-dihydro-[1,2,4]-triazol-1-yl)-4-fluorophenyl]propionate. Other analogs, homologs or derivatives of carfentrazone ethyl that may find utility in the methods of the present invention include the following:

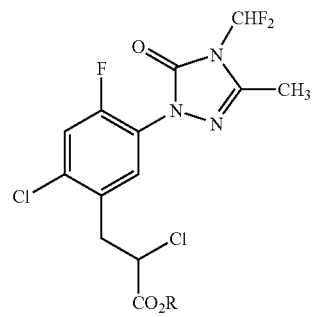

where R is selected from $CH_3$, $CH_2CH_2CH_3$, $CH(CH_3)_2$, $(CH_2)_3CH_3$, $CH_2CH(CH_3)_2$, n-pentyl, n-hexyl, $Na^+$, $K^+$, $Li^+$, $Ca^+$, and $NH_4^+$.

Carfentrazone ethyl, the metabolites, analogs, homologs or derivatives useful herein may be prepared by the methods taught in U.S. Pat. No. 5,125,958, the disclosure of which is incorporated herein by reference, or by methods analogous thereto, or by methods known to one skilled in the art.

A preferred amount of the PPO-inhibiting compound is in the range from 0.001 to 0.010 pound active ingredient per acre. A more preferred amount of the PPO-inhibiting compound is in the range from 0.002 to 0.008 pound active ingredient per acre. An even more preferred amount of the PPO-inhibiting compound is in the range from 0.004 to 0.008 pound active ingredient per acre.

As set forth above, compositions comprising HGR compounds find utility as chemical growth regulators of cotton plants in the present invention. Examples of plant growth regulating compounds which may be used in the present invention include, without limitation, dimethipin; 2,3-dihydro-5,6-dimethyl-1,4-dithiin-1,1,4,4-tetraoxide and tribufos; S,S,S-tributyl phosphorotrithioate.

A preferred amount of the HGR compound is in the range from 0.1 to 1.0 pound active ingredient per acre. A more preferred amount of the HGR compound is in the range from 0.1 to 0.25 pound active ingredient per acre.

As set forth above, compositions comprising CMD compounds and their agriculturally-acceptable salts find utility as chemical growth regulators of cotton plants in the present invention. An example of a CMD compounds which may be used in the present invention is paraquat; 1,1'-dimethyl-4,4'-bipyridinium dichloride.

A preferred amount of the CMD compound is in the range from 0.1 to 1.0 pound active ingredient per acre. A more preferred amount of the HGR compound is in the range from 0.1 to 0.25 pound active ingredient per acre.

As set forth above, compositions comprising an AAS-inhibiting compound and their agriculturally-acceptable salts find utility as chemical growth regulators of cotton plants in the present invention. An example of an AAS-inhibiting compound which may be used in the present invention is glyphosate; N-(phosphonomethyl)glycine isopropylamine salt.

A preferred amount of the AAS-inhibiting compound is in the range from 0.1 to 1.0 pound active ingredient per acre. A more preferred amount of the AAS-inhibiting compound is in the range from 0.1 to 0.25 pound active ingredient per acre.

Yet another embodiment of the present invention is the combination of a PPQ-inhibitor compound, a HGR compound, a CMD compound or an AAS-inhibiting compound and a second compound selected from a pesticide active ingredient formulation, plant nutrient formulation, plant growth hormone product or surfactant products. Surfactant products may include, but are not limited to, non ionic surfactants, cationic surfactants, crop oil concentrates, drift control additives and buffering agents.

As used in this specification and unless otherwise indicated the terms "protoporphyrinogen oxidase enzyme-inhibiting", "protoporphyrinogen oxidase enzyme-inhibitor", "PPO-inhibiting" or "PPO-inhibitor" as these terms relate to the compounds of the present invention as set forth herein are one and the same. The terms "cotton plant growth regulator" or "growth regulator" are defined as a means to artificially, using compounds and methods, cause a cotton plant to grow more productively from a yield and quality perspective.

One skilled in the art will, or course, recognize that the formulation and mode of application of the cotton plant growth regulator may affect the activity of the material in a given application. Thus, for use in cotton plant growth regulation, the cotton plant growth regulating compound may be formulated as water-soluble or water-dispersible granules, as powdery dusts, as wettable powders, as emulsifiable concentrates, as solutions, or as any of several other known types of formulations, depending on the desired mode of application. It is to be understood that the application quantities in this specification are intended to be approximate only, as if the word "about" were placed in front of the amounts specified.

The cotton plant growth regulating compositions may be applied either as water-diluted sprays, dusts or granules to the crops in which control of terminal growth is desired. These formulations may contain as little as 0.1%, 0.2% or 0.5% to as much as 95% or more by weight of the cotton plant growth regulating compound.

Dusts are free flowing admixtures of the cotton plant growth regulating compound with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the cotton plant growth regulating compound and 99.0 parts of talc. Such dust formulations are applied in this form directly to the area to be treated for cotton plant growth regulation applications.

Wettable powders are in the form of finely divided particles, which disperse readily in water or other dispersant. The wettable powder is ultimately applied either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of the cotton plant growth regulating compound, depending on the absorbency of the carrier, and usually also contain a small amount of a wetting, dispersing or emulsifying agent to facilitate dispersion. For example, a useful wettable powder formulation contains 80.0 parts of the cotton plant growth regulating compound, 17.9 parts of Palmetto clay, and 1.0 part of sodium lignosulfonate and 0.3 part of sulfonated aliphatic polyester as wetting agents. Wettable powder formulations are dispersed in water or other liquid carrier and applied as a spray to the area to be treated for cotton plant growth regulation applications.

Other useful formulations for these cotton plant growth regulation applications are emulsifiable concentrates (ECs) which are homogeneous liquid compositions dispersible in water or other dispersant, and may consist entirely of the cotton plant growth regulating compound and a liquid or solid emulsifying agent, or may also contain a liquid carrier, such as xylene, heavy aromatic naphthas, isophorone, or other non-volatile organic solvents. Emulsifiable concentrates are dispersed in water or other liquid carrier and applied as a spray to the area to be treated for cotton plant growth regulation applications. The percentage by weight of the cotton plant growth regulating compound may vary according to the manner in which the composition is to be applied, but in general comprises 0.5 to 95% of the cotton plant growth regulating compound by weight of the composition.

Flowable formulations are similar to ECs except that the cotton plant growth regulating compound is suspended in a liquid carrier, generally water. Flowables, like ECs, may include a small amount of a surfactant, and will typically contain cotton plant growth regulating compounds in the range of 0.5 to 95%, frequently from 10 to 50%, by weight of the composition. Flowables are diluted in water or other liquid vehicle, and are applied as a spray to the area to be treated for cotton growth regulator applications.

Typical wetting, dispersing or emulsifying agents used in these formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long chain mercaptans and ethylene oxide. Many other types of useful surface-active agents are available in commerce. Surface-active agents, when used, normally comprise from 1 to 15% by weight of the composition.

Still other useful formulations for cotton plant growth regulation applications include simple solutions of the cotton plant growth regulating compound in a solvent in which it is completely soluble at the desired concentration, such as acetone, alkylated naphthalenes, xylene, or other organic solvents. Pressurized sprays, typically aerosols wherein the cotton plant growth regulating compound is dispersed in finely divided form as a result of vaporization of a low-boiling dispersant solvent carrier may also be used. Water-soluble or water-dispersible granules are free-flowing, non-dusty, and readily water-soluble or water-miscible. In use in the field, the granular formulations, emulsifiable concentrates, flowable concentrates, solutions, etc., may be diluted with water to give a concentration of the cotton plant growth regulating compound in the range of from 0.1% or 0.2% to 1.5% or 2%.

The following example further illustrates the present invention, but, of course, should not be construed as in any way limiting its scope. The example includes a protocol for the evaluation of certain compounds as cotton plant growth regulators, and sets forth certain data indicating the effectiveness of such compounds. In all trials commercially available formulations of the test compounds were used as follows: carfentrazone-ethyl, AIM™ EC Herbicide from FMC Corporation; pyraflufen ethyl, ET® Herbicide/Defoliant from Nichino America, Inc.; flumiclorac-pentyl, Resource® Herbicide from Valent; fluthiacet-methyl, an EC formulation from Crompton Crop Protection; dimethipin, Harvade®-5F Harvest Growth Regulant form Crompton Crop Protection; tribufos, Def® 6 Emulsifiable Defoliant from Bayer CropScience; paraquat, Gramoxone Inteon™ Herbicide from Syngenta Crop Protection; glyphosate, Roundup® from Monsanto Company.

Example

Evaluation of Carfentrazone-ethyl, Pyraflufen ethyl, Flumiclorac-pentyl, Fluthiacet-methyl, Dimethipin, Tribufos, Paraquat and Glyphosate as Cotton Growth Regulators The trial was performed on cotton, variety D&PL 555. The formulated test compounds were diluted to the appropriate concentrations with water to which a crop oil concentrate (1% to 2% v/v) or a non-ionic surfactant (0.25% v/v) was added. The application of the test composition as a cotton plant growth regulator was performed using pressurized, over-the-top spray equipment consisting of a research scale boom sprayer. Deposit of the test composition was primarily to the top of the cotton plants, minimizing spray deposition to lower branches, leaves and fruit. The finished spray volume was 10 gallons per acre, with sprayer nozzle design, orientation and nozzle pressures chosen to prevent spray drift. Applications were made at first sign of cotton boll opening and at 15%, 20% and 40% open bolls.

The experimental design used randomized plots with 1 to 4 treatment rates of test composition and from 1 to 10 replications depending on the test (sees tables below). The size of each experimental plot was about 15 m². Testing was performed in Texas, North Carolina, Mississippi and Georgia.

Percent desiccation, percent defoliation, percent terminal control and percent open bolls were evaluated at 7 and 14 days after application (DAA) of the test composition. Inspection of cotton plants for insect control of armyworm larvae was performed at 2 DAA and insect damage to bolls was performed at the time of harvest Desiccation refers to leaves or portions of leaves dried to debris following tissue death. Percent desiccation rating approximates the proportion of leaves of all sizes killed or significantly affected by a treatment per 100 live leaves present before treatment. An evaluation of the condition of leaves in the untreated check plots were observed. Then the test plots were individually evaluated. The percent of all leaves completely or partially desiccated by the test application were recorded, based upon live leaves and leaf debris within the test plot relative to foliage present in the untreated plot.

Defoliation refers to removal of leaves. Percent defoliation rating approximates the proportion of leaves of all sizes shed per 100 leaves present prior to application of the cotton growth regulator compound. An evaluation of the foliage in the untreated check plots was first undertaken. Then the test plots were individually evaluated. The percent of leaves dropped by the plants in the treated plot was determined using observations within the plot and comparisons to foliage in the untreated plot.

Terminal control refers to crop response to the top-most vertical bud and shoots growth. Percent terminal control estimates the proportion of these upper-most growth structures desiccated per 100 cotton plants. Fifty cotton plants in two representative locations within a treatment plot were chosen to determine percent control. Each terminal of the 50 plants in the 2 locations was evaluated, and the total number desiccated per 100 plants was recorded as percent terminal control.

Open bolls refers to the number of bolls which have opened per 100 cotton plants. Fifty cotton plants in two representative locations within a treatment plot were chosen to examine for open bolls. The percent of open bolls was calculated by dividing the number of open bolls by the total number of bolls on the plants multiplied by 100.

Bollworm (*Heliothis zea*) and stinkbug (*Euschistus servus*) insect control was measured by examining the bolls of 100 cotton plants, 50 cotton plants in two representative locations with in the treatment plot, for injury caused by either bollworms or by stinkbugs. The percent damage was calculated by dividing the number of damaged bolls by the total number of bolls on the plants multiplied by 100.

The presence of fall armyworms (*Spodoptera frugiperda*) was determined by examining 20 cotton plants within each of 3 replicates of the treatment plots for fall armyworm. The number of insects per plant was calculated by dividing the total number of insects found by 60.

The results, shown as the mean of the indicated number of replications, were compared with results observed in the same trials with an untreated control. The results and comparison are in the tables below.

TABLE 1

% Terminal Control at First Open Boll Application
(3 replicates)

| Treatment | Rate (lb ai/a) | 7 DAA % Terminal Control | 14 DAA % Terminal Control |
|---|---|---|---|
| carfentrazone-ethyl | 0.002 | 27 | 44 |
| carfentrazone-ethyl | 0.004 | 46 | 58 |
| carfentrazone-ethyl | 0.006 | 47 | 59 |
| carfentrazone-ethyl | 0.008 | 50 | 58 |
| Check (untreated) | — | 5 | 5 |

TABLE 2

% Terminal Control at 15% Open Boll Application
(9 replicates)

| Treatment | Rate (lb ai/a) | 14 DAA % Terminal Control |
|---|---|---|
| carfentrazone-ethyl | 0.004 | 63 |
| carfentrazone-ethyl | 0.006 | 74 |
| carfentrazone-ethyl | 0.008 | 79 |
| carfentrazone-ethyl | 0.01 | 82 |
| Check (untreated) | — | 9 |

TABLE 3

% Terminal Control at 20% Open Boll Application
(2 replicates)

| Treatment | Rate (lb ai/a) | 7 DAA % Terminal Control | 14 DAA % Terminal Control |
|---|---|---|---|
| carfentrazone-ethyl | 0.002 | 50 | 49 |
| carfentrazone-ethyl | 0.004 | 67 | 64 |
| carfentrazone-ethyl | 0.006 | 66 | 64 |
| carfentrazone-ethyl | 0.008 | 60 | 63 |
| Check (untreated) | — | 5 | 5 |

TABLE 4

% Defoliation at First Open Boll Application
(4 replicates)

| Treatment | Rate (lb ai/a) | 7 DAA % Defoliation | 14 DAA % Defoliation |
|---|---|---|---|
| carfentrazone-ethyl | 0.002 | 6 | 15 |
| carfentrazone-ethyl | 0.004 | 12 | 25 |
| carfentrazone-ethyl | 0.006 | 13 | 28 |
| carfentrazone-ethyl | 0.008 | 12 | 23 |
| Check (untreated) | — | 5 | 11 |

TABLE 5

% Defoliation at 15% Open Boll Application
(10 replicates)

| Treatment | Rate (lb ai/a) | 14 DAA % Defoliation |
|---|---|---|
| carfentrazone-ethyl | 0.004 | 28 |
| carfentrazone-ethyl | 0.006 | 33 |
| carfentrazone-ethyl | 0.008 | 39 |
| carfentrazone-ethyl | 0.01 | 41 |
| Check (untreated) | — | 17 |

TABLE 6

% Defoliation at 20% Open Boll Application
(3 replicates carfentrazone-ethyl, 1 replicate glyphosate,
paraquat, dimethipin and tribufos)

| Treatment | Rate (lb ai/a) | 7 DAA % Defoliation | 14 DAA % Defoliation |
|---|---|---|---|
| carfentrazone-ethyl | 0.002 | 9 | 17 |
| carfentrazone-ethyl | 0.004 | 25 | 38 |
| carfentrazone-ethyl | 0.006 | 22 | 34 |
| carfentrazone-ethyl | 0.008 | 24 | 36 |
| Check (untreated) | — | 7 | 13 |
| glyphosate | 0.5 | — | 7 |
| Check (untreated) | — | — | 6 |
| paraquat | 0.13 | — | 8 |
| Check (untreated) | — | — | 6 |
| tribufos | 0.14 | 30 | — |
| Check (untreated) | — | 25 | — |
| dimethipin | 0.23 | 28 | — |
| Check (untreated) | — | 25 | — |

TABLE 7

% Defoliation at 40% Open Boll Application
(1 replicate)

| Treatment | Rate (lb ai/a) | 7 DAA % Defoliation |
|---|---|---|
| carfentrazone-ethyl | 0.004 | 61 |
| carfentrazone-ethyl | 0.006 | 58 |
| carfentrazone-ethyl | 0.008 | 67 |
| Check (untreated) | — | 30 |

TABLE 8

% Desiccation at First Open Boll Application
(4 replicates for Carfentrazone-ethyl, 3 replicates for
pyraflufen ethyl and flumiclorac pentyl ester,
1 replicate for fluthiacet-methyl)

| Treatment | Rate (lb ai/a) | 7 DAA % Desiccation | 14 DAA % Desiccation |
|---|---|---|---|
| carfentrazone-ethyl | 0.002 | 15 | 18 |
| carfentrazone-ethyl | 0.004 | 25 | 25 |
| carfentrazone-ethyl | 0.006 | 28 | 28 |
| carfentrazone-ethyl | 0.008 | 33 | 32 |
| Check (untreated) | — | 0 | 5 |
| pyraflufen-ethyl | 0.0008 | 13 | 11 |
| pyraflufen-ethyl | 0.0016 | 19 | 13 |
| Check (untreated) | — | 0 | 0 |
| flumiclorac-pentyl ester | 0.027 | 16 | 13 |
| flumiclorac-pentyl ester | 0.04 | 19 | 12 |
| Check (untreated) | — | 0 | 0 |
| fluthiacet-methyl | 0.0018 | 25 | 17 |
| Check (untreated) | — | 0 | 0 |

TABLE 9

% Desiccation at 15% Open Boll Application
(10 replicates)

| Treatment | Rate (lb ai/a) | 14 DAA % Desiccation |
|---|---|---|
| carfentrazone-ethyl | 0.004 | 29 |
| carfentrazone-ethyl | 0.006 | 33 |
| carfentrazone-ethyl | 0.008 | 37 |
| carfentrazone-ethyl | 0.01 | 38 |
| Check (untreated) | — | 18 |

TABLE 10

% Desiccation at 20% Open Boll Application
(3 replicates @ 7 DAA, 2 replicates @ 14 DAA carfentrazone-ethyl,
1 replicate glyphosate,
paraquat, dimethipin and tribufos)

| Treatment | Rate (lb ai/a) | 7 DAA % Desiccation | 14 DAA % Desiccation |
|---|---|---|---|
| carfentrazone-ethyl | 0.002 | 8 | 13 |
| carfentrazone-ethyl | 0.004 | 17 | 23 |
| carfentrazone-ethyl | 0.006 | 21 | 22 |
| carfentrazone-ethyl | 0.008 | 24 | 22 |
| Check (untreated) | — | 0 | 0 |
| glyphosate | 0.5 | — | 67 |
| Check (untreated) | — | — | 60 |
| paraquat | 0.13 | — | 90 |
| Check (untreated) | — | — | 60 |
| tribufos | 0.14 | 78 | — |
| Check (untreated) | — | 27 | — |
| dimethipin | 0.23 | 40 | — |
| Check (untreated) | — | 27 | — |

TABLE 11

% Desiccation at 40% Open Boll Application
(1 replicate)

| Treatment | Rate (lb ai/a) | 7 DAA % Desiccation |
|---|---|---|
| carfentrazone-ethyl | 0.004 | 6 |
| carfentrazone-ethyl | 0.006 | 5 |
| carfentrazone-ethyl | 0.008 | 9 |
| Check (untreated) | — | 0 |

TABLE 12

% Open Bolls at First Open Boll Application
(3 replicates)

| Treatment | Rate (lb ai/a) | 14 DAA % Open Bolls |
|---|---|---|
| carfentrazone-ethyl | 0.002 | 61 |
| carfentrazone-ethyl | 0.004 | 58 |
| carfentrazone-ethyl | 0.006 | 63 |
| carfentrazone-ethyl | 0.008 | 68 |
| Check (untreated) | — | 58 |

TABLE 13

% Open Bolls at 15% Open Boll Application
(10 replicates)

| Treatment | Rate (lb ai/a) | 14 DAA % Open Bolls |
|---|---|---|
| carfentrazone-ethyl | 0.004 | 59 |
| carfentrazone-ethyl | 0.006 | 61 |
| carfentrazone-ethyl | 0.008 | 64 |
| carfentrazone-ethyl | 0.01 | 63 |
| Check (untreated) | — | 54 |

TABLE 14

% Open Bolls at 20% Open Boll Application
(3 replicates)

| Treatment | Rate (lb ai/a) | 14 DAA % Open Bolls |
|---|---|---|
| carfentrazone-ethyl | 0.002 | 62 |
| carfentrazone-ethyl | 0.004 | 62 |
| carfentrazone-ethyl | 0.006 | 67 |
| carfentrazone-ethyl | 0.008 | 62 |
| Check (untreated) | — | 58 |

TABLE 15

% Bolls Damaged by Bollworm (*Heliothis zea*) at 15%
Open Boll Application
(1 replicate)

| Treatment | Rate (lb ai/a) | At Harvest % Bolls Damaged |
|---|---|---|
| carfentrazone-ethyl | 0.006 | 1.75 |
| Mustang Max* | 0.025 | 1.75 |
| Check (untreated) | — | 3.5 |

*Mustang Max is the commercially available formulation of zeta-cypermethrin from FMC Corporation

TABLE 16

% Bolls Damaged by Brown Stinkbug (*Euschistus servus*)
at 15% Open Boll Application
(1 replicate)

| Treatment | Rate (lb ai/a) | At Harvest % Bolls Damaged |
|---|---|---|
| carfentrazone-ethyl | 0.006 | 2.25 |
| Mustang Max* | 0.025 | 1.5 |
| Check (untreated) | — | 5.75 |

*Mustang Max is the commercially available formulation of zeta-cypermethrin from FMC Corporation

TABLE 17

Number of Fall Armyworms (*Spodoptera frugiperda*) at 15%
Open Boll Application
(3 replicates)

| Treatment | Rate (lb ai/a) | 2 DAA Number of insects |
|---|---|---|
| carfentrazone-ethyl | 0.004 | 0 |
| Check (untreated) | — | 5.33 |

TABLE 18

Cotton yield using Carfentrazone-ethyl
(5 replicates)

| Treatment Application | Rate (lb ai/a) | Lb lint/Acre |
|---|---|---|
| First open boll | 0.002 | 1172 |
| First open boll | 0.004 | 1004 |
| First open boll | 0.006 | 1152 |
| First open boll | 0.008 | 1167 |
| 20% open bolls | 0.002 | 1168 |
| 20% open bolls | 0.004 | 1128 |
| 20% open bolls | 0.006 | 1107 |
| 20% open bolls | 0.008 | 1178 |
| Check (untreated) | — | 1081 |

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for controlling terminal growth of a cotton plant, which comprises applying from 0.0005 pound active ingredient per acre to 0.025 pound active ingredient per acre of carfentrazone-ethyl to a cotton plant at a time between the opening of a first cotton boll and the opening of 40% of the bolls.

2. The method of claim 1, wherein the amount of carfentrazone-ethyl is in the range of from 0.002 pound active ingredient per acre to 0.008 pound active ingredient per acre.

3. The method of claim 1, wherein the amount of carfentrazone-ethyl is in the range of from 0.004 pound active ingredient per acre to 0.008 pound active ingredient per acre.

4. The method of claim 1, wherein the carfentrazone-ethyl is applied at a time between the opening of a first cotton boll and the opening of 20% of the bolls.

5. The method of claim 1, wherein the carfentrazone-ethyl is applied at a time between the opening of 15% and the opening of 20% of the bolls.

6. The method of claim 1, wherein the carfentrazone-ethyl is applied topically on foliage, including the terminal growth, of a cotton plant.

7. The method of claim 1, wherein a second compound selected from the group consisting of a pesticide active ingredient formulation, a plant nutrient formulation, a plant growth hormone product and a surfactant product is applied together with carfentrazone ethyl.

8. The method of claim 7, wherein said surfactant product is selected from the group consisting of a non ionic surfactant, a crop oil concentrate, a drift control additive and a buffering agent.

* * * * *